United States Patent [19]

Rose et al.

[11] Patent Number: 4,842,612
[45] Date of Patent: Jun. 27, 1989

[54] AMINOPHENYL ALKYLENEDIAMINES USEFUL IN OXIDATION HAIR DYES

[75] Inventors: David Rose, Hilden; Edgar Lieske, Duesseldorf; Norbert Maak, Neuss, all of Fed. Rep. of Germany

[73] Assignee: Henkel Kommanditgesellschaft auf Aktien, Duesseldorf, Fed. Rep. of Germany

[21] Appl. No.: 172,106

[22] Filed: Mar. 23, 1988

[30] Foreign Application Priority Data

Apr. 6, 1987 [DE] Fed. Rep. of Germany ....... 3711579

[51] Int. Cl.⁴ .......................... A61K 7/13; C07C 87/50
[52] U.S. Cl. ............................................ 8/411; 8/406; 8/408; 8/410; 8/416; 564/305; 564/443
[58] Field of Search ................... 8/406, 408, 410, 411, 8/416; 564/305, 443

[56] References Cited

U.S. PATENT DOCUMENTS

| | | | |
|---|---|---|---|
| 3,694,138 | 9/1972 | Kalopissis et al. | 8/408 |
| 4,010,200 | 3/1977 | Kalopissis et al. | 260/570 |
| 4,054,147 | 10/1977 | Kalopissis et al. | 8/408 |
| 4,200,432 | 4/1980 | Kalopissis et al. | 8/408 |
| 4,314,809 | 2/1982 | Rose et al. | 8/406 |
| 4,325,704 | 4/1982 | Konrad et al. | 8/406 |
| 4,371,370 | 2/1983 | Rose et al. | 8/408 |
| 4,381,920 | 5/1983 | Garlen | 8/406 |
| 4,555,246 | 11/1985 | Grollier et al. | 8/406 |
| 4,629,466 | 12/1986 | Rose et al. | 8/408 |

Primary Examiner—Paul Lieberman
Assistant Examiner—Helene Kirschner
Attorney, Agent, or Firm—Ernest G. Szoke; Wayne C. Jaeschke; Norvell E. Wisdom, Jr.

[57] ABSTRACT

N-4-aminophenyl-N'-2,4-diaminophenyl alkylenediamines corresponding to the formula

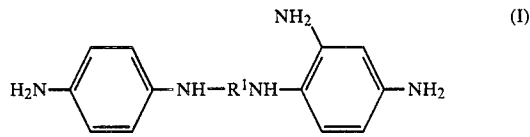

and water-soluble salts thereof. The above compounds are suitable as developers in oxidation hair dyes. Such hair dyes contain compounds corresponding to formula (I) or salts thereof as developer component in addition to conventional developer and conventional coupler components and, optionally, conventional substantive hair dyes in a cosmetic carrier. In conjunction with phenols, naphthols, resorcinols and 1,3-bis-(2,4-diaminophenyl)-alkanes or 1,3-bis-(2,4-diaminophenoxy)-alkanes as couplers, the new developers give particularly intensive colors with good light fastness properties.

25 Claims, No Drawings

AMINOPHENYL ALKYLENEDIAMINES USEFUL IN OXIDATION HAIR DYES

BACKGROUND OF THE INVENTION

1. Field of the Invention

This invention relates to new aminophenyl alkylenediamines and salts thereof and to their use as developer components in oxidation hair dyes.

2. Statement of Related Art

By virtue of their intense colors and good fastness properties, oxidation hair dyes play a prominent part in the dyeing of hair. Hair dyes such as these contain oxidation dye precursors in a cosmetic carrier. Developer substances and coupler substances are used as the oxidation dye precursors. The developer components form the actual dyes with one another or by coupling with one or more coupler components under the effect of oxidizing agents or atmospheric oxygen.

Good oxidation dye precursors have to satisfy various requirements. They must form the required shades with sufficient intensity during the oxidative coupling reaction. They must be readily absorbed by human hair with no significant differences in this regard between neglected and freshly washed hair. They should be stable to light, heat and the effect of chemical reducing agents especially when in the form of liquid hair dye preparations. Finally, they should not excessively stain the scalp and, above all, should be toxicologically and dermatologically safe to use.

The developer substances conventionally used include primary aromatic amines containing another free or substituted hydroxy or amino moiety in the para or ortho position, diaminopyridine derivatives, heterocyclic hydrazine derivatives and 4-aminopyrazolone derivatives. Useful conventional coupler substances include m-phenylenediamine derivatives, naphthols, resorcinol derivatives and pyrazolones.

Particular importance is attributed to the intensity of the colors formed during the oxidative coupling reaction and to the fastness properties, more especially fastness to light. N,N'-bix-(4-aminophenyl)-ethylenediamines are already known as oxidation dye precursors in hair dyes from U.S. Pat. No. 4,010,200. However, the hair colors obtainable with these developer components in conjunction with standard coupler comounds do not satisfy the stringent requirements of the industry in regard to intensity and fastness properties.

DESCRIPTION OF THE INVENTION

Other than in the operating examples, or where otherwise indicated, all numbers expressing quantities of ingredients or reaction conditions used herein are to be understood as modified in all instances by the term "about".

It has now been found that considerably more intensive hair colors can be obtained by using N-4-aminophenyl-N'-2,4-diaminophenyl alkylenediamines as a developer component.

The present invention also provides novel N-4-aminophenyl-N'-2,4-diaminophenyl alkylenediamines, per se, corresponding to the formula:

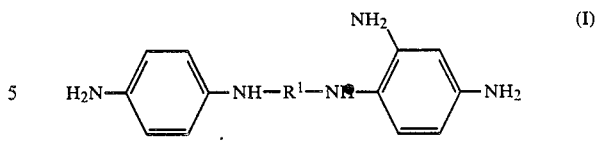

wherein: $R^1$ is $-C_nH_{2n}-$, where n is 2 to 4, or

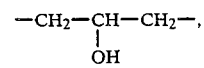

and water soluble salts thereof. Among the compounds corresponding to this formula, N-4-aminophenyl-N'-2,4-diaminophenyl ethylenediamine is the most important.

The new compounds corresponding to formula (I) may be prepared by a basically standard process in which N-(p-nitrophenyl)-alkylendediamines corresponding to the formula:

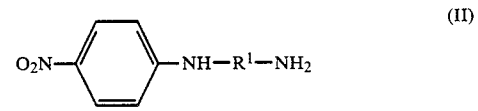

wherein $R^1$ is as defined for formula I, are reacted with 2,4-dinitrofluorobenzene and the N-4-nitrophenyl-N'-2,4-dinitrophenyl alkyenediamine obtained is catalytically hydrogenated to the N-4-aminophenyl-N'-2,4-diaminophenyl alkylenediamine corresponding to formula (I).

The new compounds corresponding to formula (I) or salts thereof either alone or in mixtures are suitable for use as oxidation dye precursors of the developer type in hair dyes. They are capable of forming dyes under the effect of oxidizing agents alone. However, particularly intensive and brilliant dyes are formed by oxidative coupling in the presence of useful conventional coupler components.

The present invention also relates to hair dyes containing oxidation dye precursors in a cosmetic carrier, which contain as oxidation dye precursors N-4-aminophenyl-N'-2,4-diaminophenyl alkylenediamines of formula (I) or water soluble salts thereof as a developer component in addition to conventional developer and coupler components and, optionally, substantive hair dyes. Among the many known conventional coupler substances, those containing phenolic hydroxyl moieties and those of the bis-(2,4-diaminophenyl)-alkane type and the bis-(2,4-diaminophenoxy)- alkane type, as described in U.S. Pat. No. 4,629,466 and in German patent document No. 28 52 272, are particularly suitable for combination with the new developers corresponding to formula (I). Accordingly, another particularly preferred embodiment of the invention comprises oxidative hair dyes containing phenols, naphthols, resorcinols and/or 1,3-bis-(2,4-diaminophenyl-alkanes or 1,3-bis-(2,4-diaminophenoxyl)-alkanes as a coupler component. Hair dyes such as these give particularly intensive and desirable colors in shades of blue-red, violet, blue and black.

The N-4-aminophenyl-N'-2,4-diaminophenyl alkylenediamines corresponding to formula (I) may be isolated and used in hair dyes either as such or in the form of their water soluble salts with inorganic or organic acids, for example as hydrochlorides, sulfates, phosphates, acetates, propionates, lactates or citrates.

The developer substances and the coupler substances are generally used in equimolar quantities in the hair dyes according to the invention, although a certain excess of individual oxidation dye precursors is not a disadvantage, so that developer substances and coupler substances may be used in a mol ratio of 1.0:0.5–2.0. The N-4-aminophenyl-N'-2,4-diaminophenyl alkylenediamines corresponding to formula (I) according to the invention or salts thereof may be used in a quantity of from 0.05–10 millimols per 100 g hair dye. The compounds corresponding to formula (I) do not have to be used as individual compounds. Instead, mixtures of the compounds may also be used.

Known substantive hair dyes, for example nitrophenylenediamine derivatives, anthraquinone dyes or indophenols, may also be added to the hair dyes according to the invention to modify the hair color.

To produce the hair dyes according to the invention, the oxidation dye precursors and, optionally, substantive dyes are incorporated in a suitable cosmetic carrier. Examples of suitable cosmetic carriers are creams, emulsions, gels, surfactant-containing foaming solutions, such as shampoos, or other preparations which are suitable for application to the hair. Standard ingredients of cosmetic preparations such as these include wetting agents and emulsifiers, such as anionic, nonionic or ampholytic surfactants, for example fatty alcohol sulfates, alkane sulfonates, alpha-olefin sulfonates, fatty alcohol polyglycol ether sulfates, ethylene oxide adducts with fatty alcohols, fatty acids and alkylphenols, sorbitan fatty acid esters and fatty acid partial glycerides, fatty acid alkanolamides, and thickeners, such as methyl or hydroxyethyl cellulose, starch, fatty alcohols, paraffin oils, fatty acids, perfume oils, and hair-care additives, such as water soluble cationic polymers, protein derivatives, pantothenic acid and cholesterol.

The ingredients of the cosmetic carriers are used in conventional quantities in the production of the hair dyes according to the invention. For example, the emulsifiers are used in concentrations of from 0.5 to 30% by weight and the thickeners in concentrations of from 0.1 to 25% by weight, based on the dye as a whole. The oxidation dye precursors (developers and couplers) are incorporated in the carrier minimally in hair-dye effective amounts, preferably in quantities of 0.2 to 5% by weight, most preferably 1 to 3% by weight, based on the dye as a whole.

One preferred formulation for the N-4-aminophenyl-N'-2,4-diaminophenyl alkylenediamines corresponding to formula (I) comprises cream hair dyes in the form of an oil-in-water emulsion containing (a) from 1 to 10 millimols per 100 g of inventive developer components, optionally mixed with conventional developer components,
(b) from 1 to 10 millimols per 100 g of conventional coupler components.
(c) from 1 to 10% by weight of a $C_{10-16}$ alkyl sulfate or $C_{10-16}$ alkyl ether sulfate surfactant,
(d) from 5 to 20% by weight of a $C_{12-18}$ fatty alcohol or $C_{12-18}$ fatty alcohol mixture,
(e) from 01. to 2.0% by weight of at least one oxidation inhibitor, preferably alkali sulfite, alkali ascorbate or alkali dithionite,
(f) ammonia q.s. to adjust the pH of the emulsion to between 8 and 10, and
(g) water q.s. to 100%

The alkyl sulfate or alkyl ether sulfate surfactant mentioned may be present as an alkali, ammonium or $C_{2-3}$ alkanolammonium salt for example as the sodium, triethanolammonium or isopropanolammonium salt. A sulfuric acid monoester salt of an adduct of 1 to 10 mols ethylene oxide with a $C_{10-16}$ fatty alcohol may be used as the alkyl ($C_{10-16}$) ether sulfate surfactant.

Basically, the hair color may be oxidatively developed with atmospheric oxygen. However, it is preferred to use a chemical oxidizing agent, particularly when it is desired not only to color, but also to lighten the hair. Particularly suitable oxidizing agents are hydrogen peroxide or adducts thereof with urea, melamine or sodium borate and also mixtures of such hydrogen peroxide adducts with potassium peroxydisulfate, present in an oxidizing effective amount.

The hair dyes according to the invention may be used in a mildly acidic, neutral or alkaline medium, irrespective of the type of cosmetic preparation used, for example a cream, gel or shampoo. The hair dyes are preferably used in the pH range from 8 to 10. They may be used at temperatures of from 15° C./ to 40° C.

After a contact time with the hair of 25–35 minutes, preferably about 30 minutes, the hair dye is removed by rinsing. The hair may then be washed with a mild shampoo and dried. Washing with a shampoo is unnecessary when a carrier of high surfactant content, for example a dye shampoo, is used.

The following Examples are intended to illustrate the invention without limiting it in any way.

EXAMPLES

1. Preparation Examples

N-4-aminophenyl-N'-2,4-diaminophenyl ethylenediamine.5 $HCl.H_2O$

[1.1] N-4-nitrophenyl-N'-2,4-dinitrophenyl ethylenediamine

A mixture of 9.05 g (0.05 mol) N-(p-nitrophenyl)-ethylenediamine, 4.2 g (0.05 mol) sodium hydrogen carbonate and 100 ml ethanol was heated to 50° C. 9.3 g (0.05 mol) 2,4-dinitrofluorobenzene were added dropwise at that temperature. After boiling under reflux for 2 hours, the mixture was cooled and the deposit filtered off. Yellow crystals melting at 242° C. were obtained.

[1.2] N-4-aminophenyl-N'-2,4-diaminophenyl ethylenediamine.5$HCl.H_2O$ 7 g of the reaction product from 1.1 were dissolved in 200 ml ethanol and hydrogenated at approximately 20° C./2 bar $H_2$ pressure in the presence of 0.5 g palladium on carbon. After hydrogen was complete, the catalyst was filtered and the filtrate (product) was acidified with hydrochloric acid and concentrated by evaporation to dryness. Violet crystals melting at 226° C. (with decomposition) were obtained.

2. Application Examples

Hair dyes according to the invention were prepared in the form of a hair dye cream emulsion having the following composition:

| | |
|---|---|
| $C_{12-14}$ fatty alcohol | 10.0 g |
| $C_{12-14}$ fatty alcohol + 2 E.O sulfate, Na salt, 28% | 25.0 g |
| Water | 60.0 g |
| N—4-aminophenyl-N'—2,4-diaminophenyl ethylenediamine.5 $HCl.H_2O$ | 7.5 mmol |
| Coupler component | 7.5 mmol |

| | |
|---|---|
| N₂SO₃ (inhibitor) | 1.0 g |
| Concentrated ammonia solution | to pH 9.5 |
| Water | q.s. to 100 g |

The constituents were mixed together in the above order. After addition of the oxidation dye precursors and the inhibitor, the pH of the emulsion was first adjusted to 9.5 with concentrated ammonia solution, after which the emulsion was made up with water to 100 g.

The hair color was oxidatively developed with 3% hydrogen peroxide solution as oxidizing agent. To this end, 50 g hydrogen peroxide solution (3%) were added and mixed with 100 g of the emulsion.

The dye cream was applied to approximately 5 cm long strands of standardized, 90% gray, but not specially pretreated human hair and left thereon for 30 minutes at 27° C. After dyeing, the hair was rinsed, washed with a standard shampoo and then dried.

The compounds shown in Table I were used as couplers in combination with the developer of Example I. The hair colors likewise shown in Table I were obtained.

The hair colors according to Examples 2.1 to 2.3 were additionally tested for fastness to light.

Testing of light fastness:

The fastness to light of the dyed hair strands was determined in accordance with DIN (German Industrial Norm) 54,004 (April 1966), Section 7.5.2 the method essentially comprises exposing the dyed hair strands alongside fabric samples with 6 fastness-graduated blue standard dyes of the fastness scale to the light of a xenon arc lamp with a color temperature of 5500 to 6500 °K. To this end, the strands and the fabric samples are fastened alongside one another to a card and the marginal zones of the strands and fabric samples are covered parallel to the longitudinal edge of the sample holder. Exposure is carried out with frequent inspection by removal of the cover plate until standard 3 of the light fastness scale shows a just noticeable difference between the exposed part of the unexposed part. The samples are then inspected for changes and the changes, if any, are evaluated by comparison with the changes in standards 1, 2 and 3 of the fastness scale. Exposure is then continued until standard 4 of the light fastness scale also shows a just noticeable difference in color between the exposed part and the unexposed part. The cover plate is then replaced by a larger cover plate which covers approximately ⅓ of the previously exposed surface parallel to the longitudinal edge. Exposure is then continued until standard 6 of the scale shows a just noticeable color difference. Light fastness is determined by comparing the contrasts on the stands of hair with the contrasts of the standard colors of the light fastness scale.

The result of the light fastness test are also shown in Table I.

TABLE I

| Example No. | Coupler component | Color obtained | Fastness |
|---|---|---|---|
| 2.1 | 1-naphthol | dark ruby | 4 |
| 2.2 | resorcinol | brown-olive | 4 |
| 2.3 | m-aminophenol | black | 4 |
| 2.4 | 5-amino-2-methylphenol | dark violet | |
| 2.5 | 5-amino-4-chloro-2-methylphenol | black violet | |
| 2.6 | 2,4-dichloro-3-aminophenol | black | |
| 2.7 | 1,3-bis-(2,4-diaminophenyl)-propane | blue black | |

All of the above obtained colors are considered desirable for hair dye purposes. Similarly the light fastness value of 4 indicates a hair dye whose light fastness is desirable for hair dye purposes.

We claim:

1. An N-4-aminophenyl-N'-2,4-diaminophenyl alkylenediamine corresponding to the formula

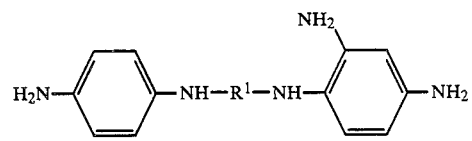

wherein R1 is: —$C_nH_{2n}$— where n is 2 to 4; or

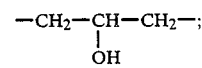

or a water soluble salt thereof.

2. N-4-aminophenyl-N'-2,4-diaminophenyl ethylenediamine; or a hydrochloride, sulfate, phosphate, acetate, propionate, lactate or citrate salt thereof.

3. The compound of claim 1 wherein $R^1$ is —$C_nH_{2n}$— and n is 3; or a hydrochloride, sulfate, phosphate, acetate, propionate, lactate, or citrate salt thereof.

4. The compound of claim 1 wherein R is —$Cd_nH_{2n}$— and n is 4; or a hydrochloride, sulfate, phosphate, acetate, propionate, lactate, or citrate salt thereof.

5. The compound of claim 1 wherein R is

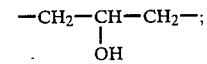

or a hydrochloride, sulfate, phosphate, acetate, propionate, lactate, or citrate salt thereof.

6. An oxidative hair dye composition comprising at least one conventional hair dye coupler and a hair dye developer consisting of at least one compound according to claim 1 and, optionally, at least one conventional hair dye developer, said coupler and developer components being present in an oxidative hair dye effective amount.

7. The composition of claim 6 further comprising a chemical oxidizing agent, present in an oxidizing effective amount.

8. The composition of claim 7 further comprising at least one substantive hair dye.

9. The composition of claim 6 wherein said developer and said coupler components are present in a mol ratio of about 1.0:0.5–2.0.

10. The composition of claim 6 wherein said coupler is at least one phenol, naphthol, resorcinol, 1,3-bis-(2,4-diaminophenyl)-alkane, or 1,3-bis-(2,4-diaminophenoxy)-alkane.

11. The composition of claim 6 wherein said coupler is at least one of: 1-naphthol; resorcinol; m-aminophenol; 5-amino-2-methylphenol; 5-amino-4-chloro-2- methylphenol; 2,4-dichloro-3-aminophenol; or 1,3-bis-(2,4-diaminophenyl)-propane.

12. The composition of claim 10 wherein said developer is N-4-aminophenyl-N'-2,4-diaminophenyl ethylenediamine, or a hydrochloride, sulfate, phosphate, acetate, propionate, lactate or citrate salt thereof.

13. The composition of claim 11 wherein said developer is N-4-aminophenyl-N'-2,4-diaminophenyl ethylenediamine, or a hydrochloride, sulfate, phosphate, acetate, propionate, lactate or citrate salt thereof.

14. The composition of claim 10 wherein said developer is the compound of claim 1 wherein $R^1$ is $-C_nH_{2n}-$ and n is 3; or a hydrochloride, sulfate, phosphate, acetate, propionate, lactate, or citrate salt thereof.

15. The composition of claim 11 wherein said developer is the compound of claim 1 wherein $R^1$ is $-C_nH_{2n}-$ and n is 3; or a hydrochloride, sulfate, phosphate, acetate, or propionate, lactate, or citrate salt thereof.

16. The composition of claim 10 wherein said developer is the compound of claim 1 wherein R is $-C_nH_{2n}-$ and n is 4; or a hydrochloride, sulfate, phosphate, acetate, propionate, lactate, or citrate salt thereof.

17. The composition of claim 11 wherein said developer is the compound of claim 1 wherein R is $-C_nH_{2n}-$ and n is 4; or hydrochloride, sulfate, phosphate, acetate, propionate, lactate, or citrate salt thereof.

18. The composition of claim 10 wherein said developer is the compound of claim 1 wherein R is

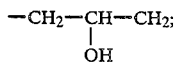

or a hydrochloride, sulfate, phosphate, acetate, propionate, lactate, or citrate salt thereof.

19. The composition of claim 11 wherein said developer is the compound of claim 1 wherein R is

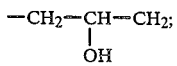

or a hydrochloride, sulfate, phosphate, acetate, propionate, lactate, or citrate salt thereof.

20. A cream oxidative hair dye oil-in-water emulsion comprising:
(a) about 1-10 millimols per 100 g of one or more oxidative hair dye developer compounds according to claim 1, optionally mixed with one or more conventional oxidative hair dye developer compounds;
(b) about 1-10 millimols per 100 g of one or more conventional oxidative hair dye coupler compounds;
(c) about 1-10 wt % of at least one $C_{10-18}$ alkyl sulfate or $C_{10-16}$ alkyl ether sulfate surfactant;
(d) about 5-20 wt % of at least one $C_{12-18}$ fatty alcohol or $C_{12-18}$ fatty alcohol mixture;
(e) about 0.1 to 2.0 wt % of at least one oxidation inhibitor;
(f) ammonia q.s. to adjust the emulsion pH to 8-10; and
(g) water q.s. to 100 weight %;
all weights based upon the entire emulsion.

21. A cream oxidative hair dye oil-in-water emulsion comprising:
(a) about 1-10 millimols per 100 g of one or more oxidative hair dye developer compounds according to claim 2, optionally mixed with one or more conventional oxidative hair dye developer compounds;
(b) about 1-10 millimols per 100 g of one or more conventional oxidative hair dye coupler compounds;
(c) about 1-10 wt % of at least one $C_{10-18}$ alkyl sulfate or $C_{10-16}$ alkyl ether sulfate surfactant;
(d) about 5-20 wt % of at least one $C_{12-18}$ fatty alcohol or $C_{12-18}$ fatty alcohol mixture;
(e) about 0.1 to 2.0 wt % of at least one oxidation inhibitor;
(f) ammonia q.s. to adjust the emulsion pH to 8-10; and
(g) water q.s. to 100 wt %;
all weights based upon the entire emulsion.

22. A method for dyeing hair comprising: applying to said hair a hair-dyeing effecting amount of the emulsion of claim 6; permitting said emulsion to remain on said hair for a hair-dyeing effective time; and rinsing said emulsion from said hair.

23. A method for dyeing hair comprising: applying to said hair a hair-dyeing effective amount of the emulsion of claim 12; permitting said emulsion to remain on said hair for a hair-dyeing effective time; and rinsing said emulsion from said hair.

24. A method for dyeing hair comprising: applying to said hair a hair-dyeing effective amount of the emulsion of claim 20; permitting said emulsion to remain on said hair for a hair-dyeing effective time; and rinsing said emulsion from said hair.

25. A method for dyeing hair comprising: applying to said hair a hair-dyeing effective amount of the emulsion of claim 21; permitting said emulsion to remain on said hair for a hair-dyeing effective time; and rinsing said emulsion from said hair.

* * * * *